US00PP18999P3

(12) United States Plant Patent
Oliver

(10) Patent No.: US PP18,999 P3
(45) Date of Patent: Jul. 1, 2008

(54) ***ANIGOZANTHOS* HYBRID PLANT NAMED 'AMBER VELVET'**

(50) Latin Name: *Anigozanthos* hybrid
Varietal Denomination: Amber Velvet

(76) Inventor: Keith Oliver, Hamersley WA (AU)

( * ) Notice: Subject to any disclaimer, the term of this patent is extended or adjusted under 35 U.S.C. 154(b) by 0 days.

(21) Appl. No.: 11/710,088

(22) Filed: Feb. 23, 2007

(65) Prior Publication Data

US 2007/0204372 P1 Aug. 30, 2007

Related U.S. Application Data

(60) Provisional application No. 60/776,540, filed on Feb. 25, 2006.

(51) Int. Cl.
*A01H 5/00* (2006.01)

(52) U.S. Cl. ..... Plt./362

(58) Field of Classification Search ..... Plt./362
See application file for complete search history.

*Primary Examiner*—Kent L Bell

(57) ABSTRACT

'AMBER VELVET' is a distinctive variety of *Anigozanthos* hybrid which is characterized by the combination of its medium plant height with an upright growth habit and a semi-erect leaf attitude, large number of flowers per inflorescence and a predominantly orange colored perianth tube.

6 Drawing Sheets

Latin name of the genus and species: The Latin name of the genus and species of the novel variety of disclosed herein is *Anigozanthos* hybrid.

Variety denomination: The inventive variety of *Anigozanthos* disclosed herein has been given the variety denomination 'AMBER VELVET'.

BACKGROUND OF THE INVENTION

The present invention relates to a new and distinct perennial variety of *Anigozanthos* hybrid, which has been given the variety denomination of 'AMBER VELVET'. Its market class is that of an ornamental plant. 'AMBER VELVET' is intended for use in landscaping and as a decorative plant.

The *Anigozanthos* hybrid variety 'AMBER VELVET' was the result of a controlled pollination between seed parent un-named *Anigozanthos* hybrid (*A. humilis*×*A. flavidus*) and pollen parent un-named *Anigozanthos* hybrid (*A. pulcherrimus*×*A. flavidus*) in 2002 in an Australian nursery in the state of Western Australia. Seed were collected and germinated in vitro during 2003. Resultant plants were tested in 200 mm pots and in ground during 2003–2004. The inventive variety was finally selected in 2004 based on plant height, plant growth vigor, flower color and flowering season. 'AMBER VELVET' is propagated asexually by micropropagation. The distinctive characteristics of the inventive 'AMBER VELVET' variety are stable from generation to generation; clones of the variety produced by asexual reproduction maintain the distinguishing characteristics of the original plant.

'AMBER VELVET' has a medium plant height including the inflorescence (range 90–110 cm) with an upright growth habit and a semi-erect leaf attitude whereas the seed parent has a short plant height (approximately 50 cm) and the pollen parent has a tall plant height (160–180 cm). 'AMBER VELVET' has a large number of flowers per inflorescence with the predominant color of the perianth tube being orange whereas the seed parent has a yellow-orange predominant perianth tube color and the pollen parent has a yellow predominant perianth tube color. Time of beginning of flowering for 'AMBER VELVET' is spring whereas the seed parent is late winter and the pollen parent is late spring to early summer.

An application for plant breeders' rights for variety 'AMBER VELVET' has been lodged with the Australian Plant Breeders' Rights Office, and was first gazetted in February 2005 under Application No. 2005/047.

SUMMARY OF THE INVENTION

'AMBER VELVET' is a distinctive variety of *Anigozanthos* hybrid which is characterized by the combination of its medium plant height with an upright growth habit and a semi-erect leaf attitude, large number of flowers per inflorescence and a predominantly orange colored perianth tube.

BRIEF DESCRIPTION OF THE FIGURES

FIG. 1 shows an 'AMBER VELVET' plant and the comparison variety 'Gold Fever'.

FIG. 2 shows an 'AMBER VELVET' plant foliage.

FIG. 3 shows an 'AMBER VELVET' flower and leaf detail to scale.

FIG. 4 shows an 'AMBER VELVET' flower and inflorescence.

FIG. 5 shows an 'AMBER VELVET' flower outer perianth tube detail.

FIG. 6 shows an 'AMBER VELVET' anther position detail.

BOTANICAL DESCRIPTION OF THE PLANT

The following is a detailed botanical description of a new and distinct variety of an *Anigozanthos* hybrid ornamental plant known as, 'AMBER VELVET'. Plant observations were made on plants grown in New South Wales, Australia. Unless indicated otherwise, the descriptions disclosed herein are based upon observations made from October 2005 to February 2006 of mature 'AMBER VELVET' plants grown in nursery pots.

Those skilled in the art will appreciate that certain characteristics will vary with older or, conversely, younger plants. 'AMBER VELVET' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on The Royal Horticultural Society Colour Chart, The Royal Horticultural Society, London, 1995 edition.

'AMBER VELVET' is a perennial *Anigozanthos* hybrid plant which resulted from a controlled pollination between seed parent un-named *Anigozanthos* hybrid (*A. humilis*×*A. flavidus*) and pollen parent un-named *Anigozanthos* hybrid (*A. pulcherrimus*×*A. flavidus*). After its selection, 'AMBER VELVET' was asexually propagated by micropropagation. 'AMBER VELVET' has a medium plant height including the inflorescence with an upright growth habit and a semi-erect leaf attitude, large number of flowers per inflorescence and predominantly orange colored perianth tube.

Growth Habit, Dimensions and Color

'AMBER VELVET' is a medium, rhizomatous plant forming an upright fan shaped tuft. Average plant height including the inflorescence is about 100 cm (range 90–110 cm), average height of foliage only is 40 cm (range 30–60 cm) and average plant spread is 40 cm in a mature plant growth in nursery or field plots in Sydney, New South Wales, Australia (observed spring 2005–summer 2006). The number of inflorescences is medium. The mature leaf length is long (range 35–40 cm) and the mature leaf width is medium to broad (approximately 18 mm in a 140 mm pot). The leaf attitude is semi-erect and the degree of leaf curvature is slightly curved. The upper and lower sides of the leaf are yellow green (approximately RHS 147A) in color (observed summer 2006). Leaf glaucosity is very weak. The degree of hairyness of the leaf margin is absent to very weakly expressed. The leaf shape is linear-slightly falcate, leaf base is cauline, leaf margin is entire, leaf apex is acute and leaf surface texture is glabrous. The leaf venation pattern is parallel; the color is the same as the rest of the leaf. The leaf attitude is semi-erect. A representative 'AMBER VELVET' plant is shown in FIG. 1.

These features and other characteristics are apparent from the description provided below.

Roots

The roots of 'AMBER VELVET' are fibrous, freely branching and white in color and are similar to other *Anigozanthos* hybrids.

Rhizomes

The rhizomes of 'AMBER VELVET' are short creating a tufted plant similar to other *Anigozanthos* hybrids.

Inflorescence

Branching of the inflorescence is present and the degree of ramification is tertiary. The length of the lowest lateral is medium (approximately 22 cm). The number of flowers per inflorescence is many, a typical plant having approximately 10 racemes per inflorescence, each with about 10 flowers (longer than 3 mm) in a 140 mm pot size (observed summer 2006). Peduncle diameter at the base is approximately 9.5 mm.

Flowers

The color of hairs on the pedicel corresponds to red (approximately RHS 47A). The perianth tube length is medium (range to 22 mm) and the width is medium (approximately 8 mm below perianth lobes) on an opening flower. Perianth tube profile is broadening evenly. The predominant color of the outer perianth tube is orange, which is a composite effect of the hair color over the ground color of the perianth tube. The number of colors on hairs on the perianth tube is one and this corresponds to red (approximately RHS 47A). The ground color of the perianth tube is yellow (approximately RHS 13A). The inner color of the perianth tube is a yellow green (RHS 144A). The inner color of the perianth tube lobes is a grayed green (RHS 191A–B). Perianth lobe length is medium (approximately 11 mm for the longest lobe) reflexing of the lobes is strong. The number of anthers at the top of the perianth is four. The color of the hairs on the ovary corresponds to red (approximately RHS 47A). The position of the stigma in relation to the anthers is above. Time to beginning of flowering is early-medium.

Comparison of 'AMBER VELVET' with Other Varieties of *Anigozanthos* hybrid

'AMBER VELVET' combines a medium plant height with an upright growth habit and a semi-erect leaf attitude, large number of flowers per inflorescence and a predominantly orange colored perianth tube compared to other *Anigozanthos* hybrids.

'AMBER VELVET' has a shorter plant height than another comparable type known as 'Gold Fever' (unpatented) with a height of 90–110 cm whereas 'Gold Fever' is 160–180 cm tall. 'AMBER VELVET' has slightly curved leaves whereas 'Gold Fever' has strongly curved leaves 'AMBER VELVET' has many flowers per inflorescence whereas 'Gold Fever' has a medium number. 'AMBER VELVET' has a medium perianth tube length whereas 'Gold Fever' has a short to medium perianth tube length. 'AMBER VELVET' has a predominant perianth tube color in the orange group whereas 'Gold Fever' has a predominant perianth tube color in the orange-red group. 'AMBER VELVET' has a spring flowering season whereas 'Gold Fever' has a spring to summer flowering season.

The combination of medium plant height with an upright growth habit and a semi-erect leaf attitude, large number of flowers per inflorescence and a predominantly orange colored perianth tube makes 'AMBER VELVET' a desirable ornamental plant suited for mass production for pot and landscape use.

Asexual Reproduction

'AMBER VELVET' was germinated as a seedling in vitro and asexually reproduced by micropropagation. Several generations have been reproduced and 'AMBER VELVET' has been observed to retain all distinguishing characteristics that were noted in the original 'AMBER VELVET' seedling. In vitro plants of 'AMBER VELVET' initiate roots in 7 to 10 days.

Environmental Tolerances

'AMBER VELVET' plants have exhibited good tolerance to rain and wind and to tolerate temperatures from 1 to about 40 degrees Celsius. 'AMBER VELVET' has moderate to good drought tolerance. 'AMBER VELVET' has moderate to good recovery with watering after severe wilting. 'AMBER VELVET' does well in sandy and gravelly soils.

Disease Resistance

'AMBER VELVET' has not been observed to be resistant to other pathogens and pests common to *Angiozanthos*. Further testing is underway.

That which is claimed is:

1. A new and distinct variety of *Anigozanthos* hybrid plant named 'AMBER VELVET', substantially as described and illustrated herein.

* * * * *

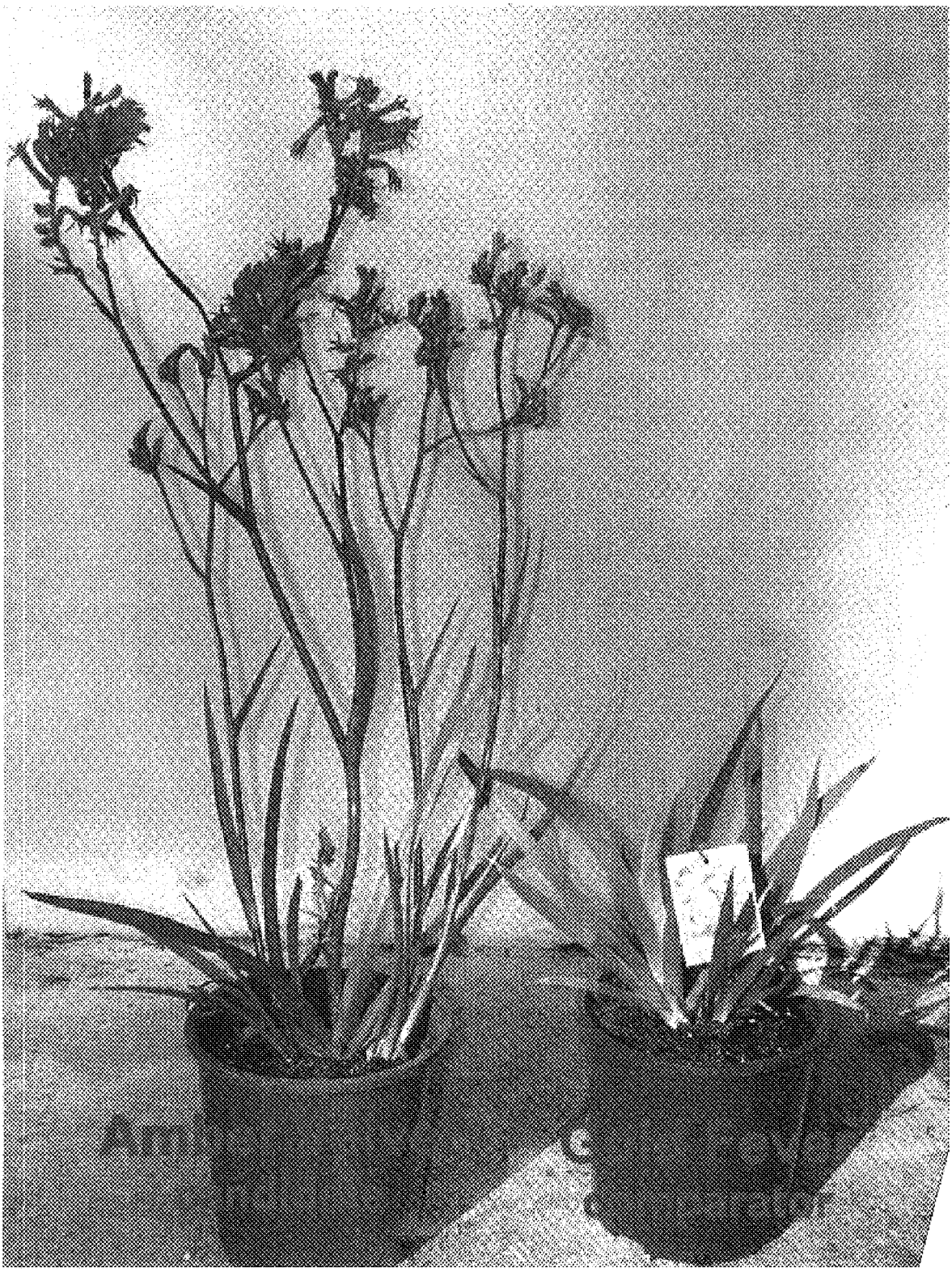

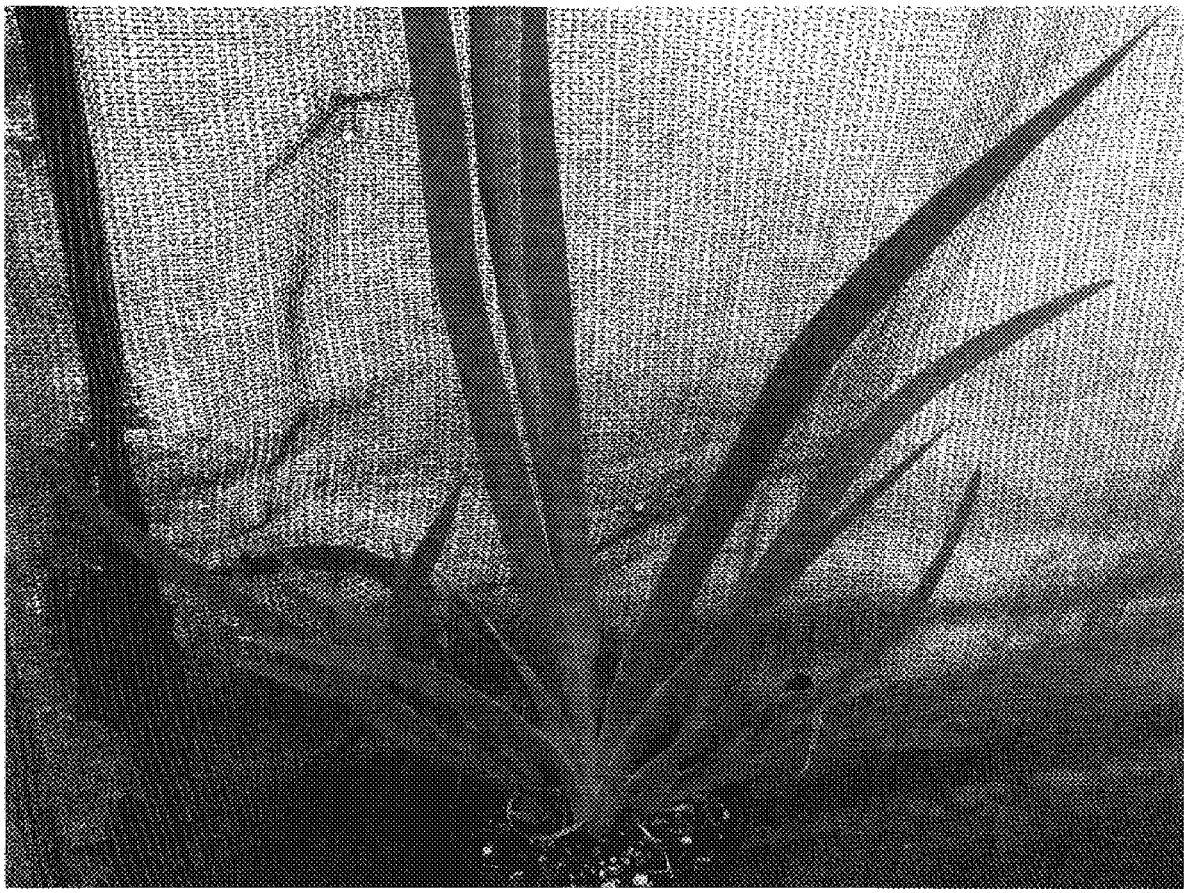

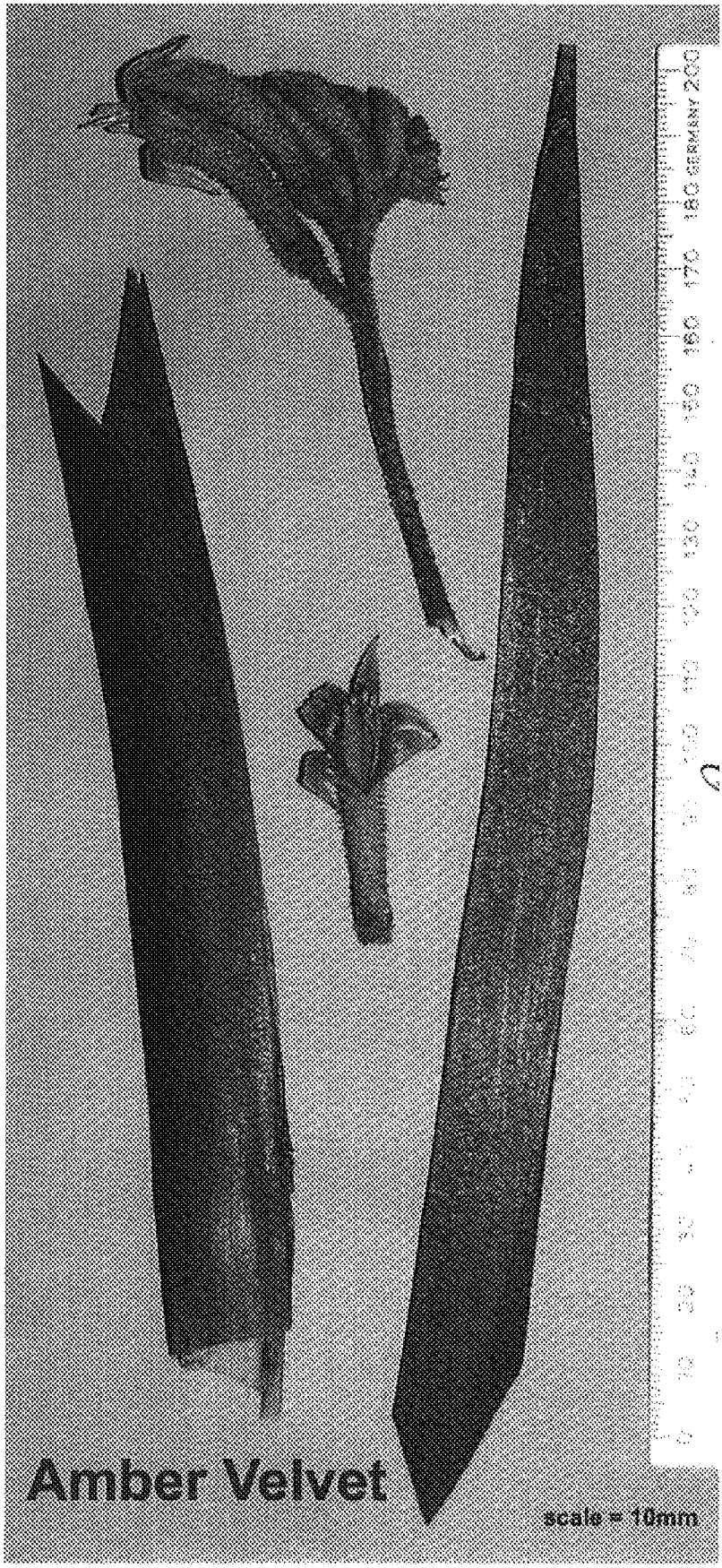
Amber Velvet
scale = 10mm

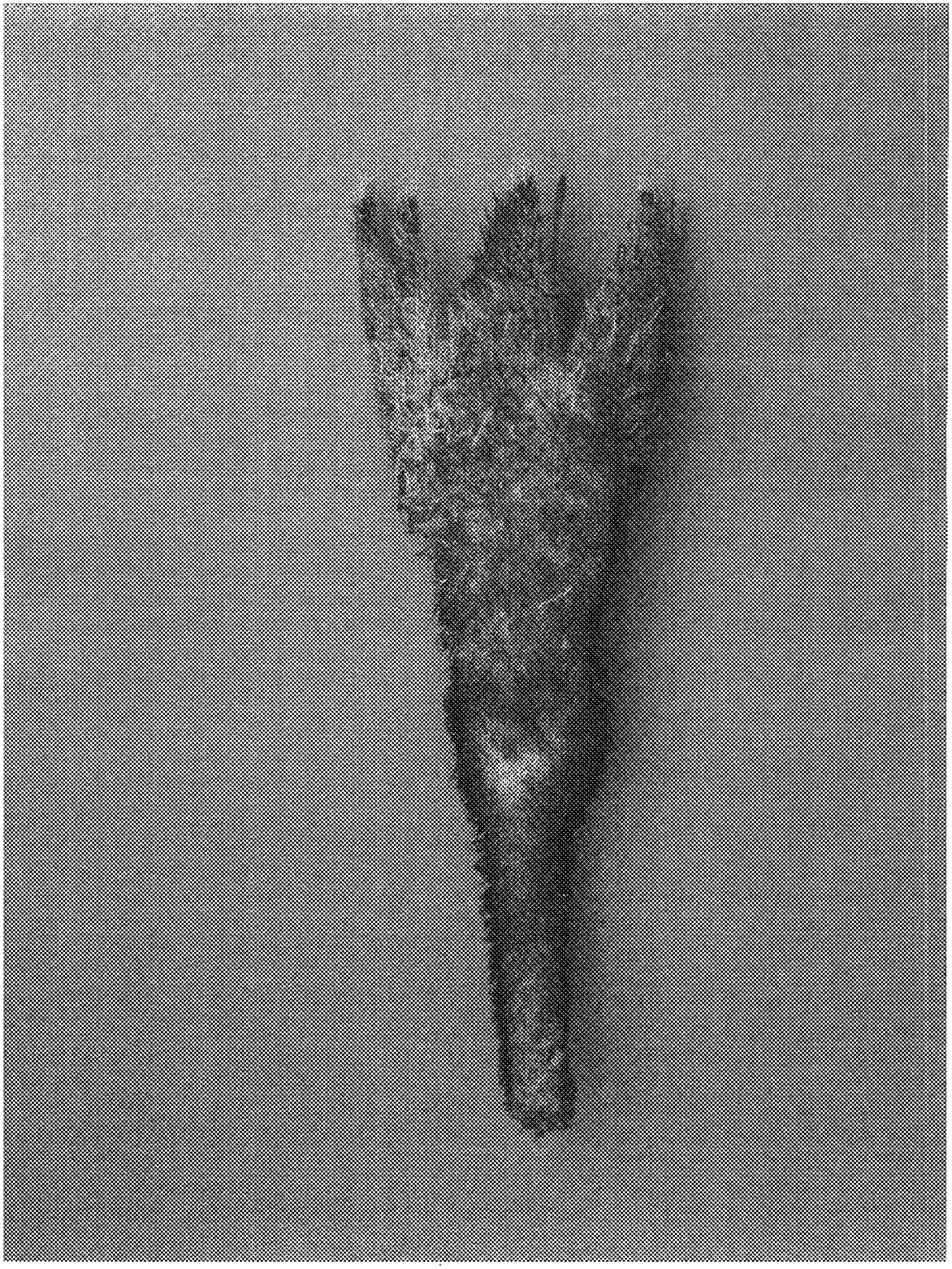

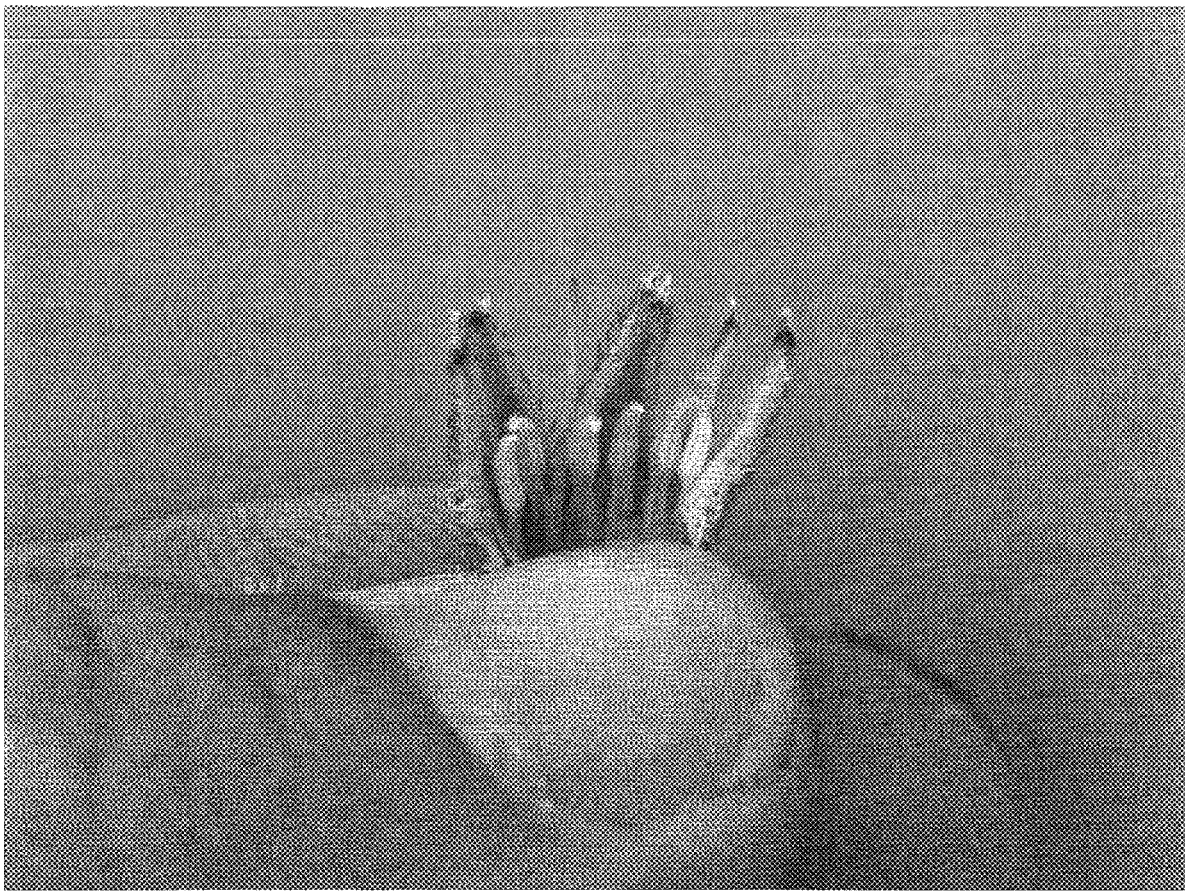

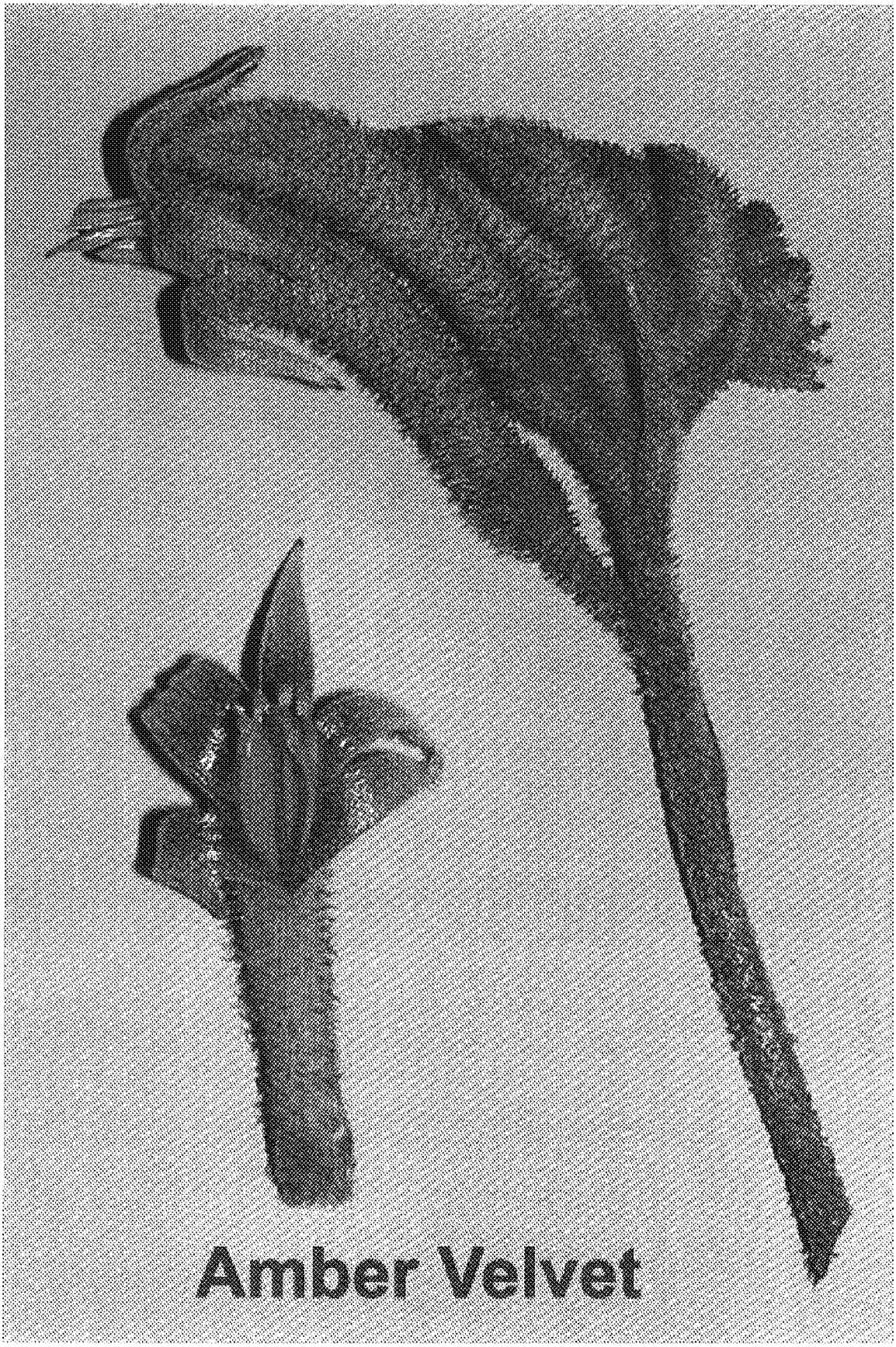
Amber Velvet